(12) United States Patent
Orfao De Matos Correia E Vale

(10) Patent No.: US 7,358,059 B2
(45) Date of Patent: Apr. 15, 2008

(54) SIMULTANEOUS QUANTIFICATION OF PIG-A ASSOCIATED PROTEINS IN RED CELLS, PLATELETS AND LEUKOCYTE SUBSETS USING A SINGLE MEASUREMENT

(75) Inventor: José Alberto Orfao De Matos Correia E Vale, Salamanca (ES)

(73) Assignee: Universidad de Salamanca, Salamanca (ES)

( * ) Notice: Subject to any disclaimer, the term of this patent is extended or adjusted under 35 U.S.C. 154(b) by 442 days.

(21) Appl. No.: 10/338,034

(22) Filed: Jan. 8, 2003

(65) Prior Publication Data

US 2003/0138851 A1    Jul. 24, 2003

Related U.S. Application Data

(60) Provisional application No. 60/346,297, filed on Jan. 9, 2002.

(51) Int. Cl.
   *G01N 33/567* (2006.01)
(52) U.S. Cl. .................. 435/7.21; 435/7.23; 435/7.24; 435/7.25; 435/973; 436/10; 436/63; 436/64; 436/172; 422/73; 422/82.05

(58) Field of Classification Search ............... 435/7.21, 435/7.23–7.25, 40.5, 973; 436/517, 548, 436/10, 63, 64, 172; 422/68.1, 82.05, 73
See application file for complete search history.

(56) References Cited

U.S. PATENT DOCUMENTS 6,287,791 B1 *  9/2001  Terstappen et al. ........ 435/7.24

OTHER PUBLICATIONS

Richards et al., Application of Flow Cytometry in the Diagnosis of Paroxysmal Nocturnal Hemoglobinuria, Cytometry 42: 223-233 (2000).*
Griscelli-Bennaceur et al., Aplastic Anemia and Paroxysmal Nocturnal Hemoglobinuria: Search for a pathogenic Link, Blood 85 (5): 1354-1363 (Mar. 1, 1995).*

* cited by examiner

*Primary Examiner*—Gailene R. Gabel
(74) *Attorney, Agent, or Firm*—Crowell & Moring LLP

(57) ABSTRACT

A single measurement can quantify phosphatidyl-inositol glycan complementation class A (PIG-A) associated proteins in red cells, platelets and the major leukocyte subsets present in blood (lymphocytes, monocytes, neutrophils and eosinophils). The single measurement relies on flow cytometry to simultaneously evaluate intensity of fluorochrome emissions and light scattering properties.

18 Claims, No Drawings

SIMULTANEOUS QUANTIFICATION OF PIG-A ASSOCIATED PROTEINS IN RED CELLS, PLATELETS AND LEUKOCYTE SUBSETS USING A SINGLE MEASUREMENT

The present invention relates generally to a procedure for the simultaneous quantification of at least two different phosphatidyl-inositol glycan complementation class A (PIG-A) associated proteins in red cells, platelets and major leukocyte subsets (including lymphocytes, monocytes, neutrophils and eosinphils) present in blood, using a single measurement.

The present invention may be understood more readily by reference to the following detailed description of particular embodiments of the invention and specific examples. The terminology used herein is for the purpose of describing particular embodiments only and is not intended to be limiting.

The present invention allows for testing of both normal and pathological samples obtained ex vivo or in vivo, including stored or treated samples. Monoclonal antibodies specific to particular proteins associated with PIG-A are used. For example, the following monoclonal antibodies known in the art can be used to practice the present invention: Anti-CD14, Anti-CD16, Anti-CD24, Anti-CD41, Anti-CD42, Anti-CD45, Anti-CD48, Anti-CD52, Anti-CD55, Anti-CD58, Anti-CD59, Anti-CD61, Anti-CD64, Anti-CD66bce, Anti-CD73, Anti-CD 87, Anti-CD90, Anti-CD108, Anti-CD109, and Anti-CD157. A common characteristic of these monoclonal antibodies is their ability to identify peripheral blood subtypes of cells, such as CD41, CD42, CD45, CD61, and CD64, or that they are PIG-A anchored surface proteins. One source for further information in this regard is *Immunobiology: The immune system in health and disease*, Appendix I, Janeway C. A., Travers P., Walport M., and Capra J. D. (Eds.), Elserior Science Ltd./ Garland Publishing, 1999.

The monoclonal antibodies are chemically coupled to fluorochromes to permit visualization and quantification of different cell types. This coupling does not alter the binding capacity of the antibodies. When activated by illumination with light of a particular wavelength, the fluorochrome-labeled antibody adsorbs the light energy, inducing a state of excitability followed by emission of light at a characteristic color.

In order to specifically identify antibody binding to cells, any compatible combination of fluorochromes can be used as well as any monoclonal antibody within each cluster of differentiation. For example, FL1 fluorescein isothiocyanate (FITC), phycoerythrin (PE), peridin chlorophyll protein (PerCP) and allophycocyanin (APC). Another example of suitable combinations of fluorochromes or fluorochrome tandems is the combination of FITC, PE, PerCP and APC-Cyanin7 (Cy7). Further examples include: FITC, PE, PerCP-Cy5 and APC; or ITC, PE, PE-Cy5 and APC, or FITC, PE, PE-Cy, PE-texas red; or FITC, PE, PE-Cy5 and APC-Cy7. The fluorochromes employed in the practice of the present invention are commercially available and understood by those of skill in the art.

In a first embodiment of the present invention, a blood sample is incubated with a mixture of monoclonal antibodies and fluorochromes as follows:

| Monoclonal Antibody Number | Antibody | Fluorochrome |
| --- | --- | --- |
| 1 | Anti-CD45 | 1 |
| 2 | Anti-CD61 or Anti-CD41 or Anti-CD42 | 1 |
| 3 | Anti-CD64 | 2 |
| 4 | Anti-CD55 | 3 |
| 5 | Anti-CD59 | 4 |

The full complement of monoclonal antibodies allows for a complete analysis of the blood sample. Monoclonal antibodies 1-3 allow for identification of red cells, platelets, and the major leukocyte subsets in the blood sample. Monoclonal antibodies 4 and 5 allow for quantification of each cell subset for the two different PIG-A associated proteins.

A patient's blood sample may be collected in a glass or plastic tube containing an anticoagulant such as EDTA, heparin or ACD. Any reasonable volume may be used, such as from 1-200 μl, the concentration of other reagents to be determined based on the volume of the sample and the saturation conditions of the reagents. The sample should be used as soon as possible, if stored it may be placed at room temperature (approximately 22° C.) or refrigerated (approximately 4° C.).

The antibody coupled to fluorochrome reagents can be purchased from a number of commercial sources. Upon addition of this reagent to the blood sample, incubation of the sample follows for approximately 30 minutes at room temperature, or for approximately 30-60 minutes under refrigeration.

Fluorescence is measured in a flow cytometer. The scale used for each measured parameter is typically a 4-logarithmic decades scale. Results are expressed in relative linear units scaled from 0 to $10^4$. The techniques and equipment utilized for fluorescence as well as light scattering measurements are well established in the art. The resultant information can De stored in digital format, making it easy to analyze several parameters for a single cell through the use of specialized software programs.

The results of the data indicate which types of cells are present in a sample based on particular characteristics. For example, red cells are identified as being CD45− and CD61− (or CD41− or CD42−) and displaying a high forward scatter (FSC) and sideward light scatter (SSC). Platelets show low FSC and SSC values and they are CD61+ (or CD41+ or CD42+). Leukocytes appear as high FSC and CD45+: from them lymphocytes show higher CD45+ values and they are CD64−; monocytes are CD64++ at very high levels, they show intermediate SSC characteristics as compared to neutrophils and eosinophils these latter cells being CD64+ with high SSC and CD64− with very high SSC values, respectively. Once these cell populations are identified, expression of PIG-A associated proteins is evaluated on each subset. The evaluation is based on both the presence or absence and the mean fluorescence intensity of unimodal or multimodal populations.

In a second embodiment of the present invention, a blood sample is incubated with a mixture of monoclonal antibodies and fluorochromes as follows:

| Monoclonal Antibody Number | Antibody | Fluorochrome |
| --- | --- | --- |
| 1 | Anti-CD45 | 2 |
| 2 | Anti-CD61 or Anti-CD41 or Anti-CD42 | 1 |
| 3 | Anti-CD64 | 1 |
| 4 | Anti-CD55 | 3 |
| 5 | Anti-CD59 | 4 |

In further embodiments of the present invention, all potential combinations of antibodies may be used. For example, CD55 and/or CD59 may be replaced by other antigens, including, but not limited to, CD14, CD16, CD24, CD48, CD52, CD58, CD66bce, CD73, CD87, CD90, CD108, CD109, and CD157.

It is also possible to follow the teaching of the present invention but to rely on only two or three different fluorochromes. This procedure may be used for analysis of a single PIG-A protein, or when quantification and analysis of a reduced number of blood cell types within a sample is necessary.

What is claimed is:

1. A method for the simultaneous quantification of the levels of expression of the CD55 and CD59 phosphatidyl-inositol glycan complementation class A (PIG-A) anchored cell membranes proteins in red cells, platelets, lymphocytes, monocytes, neutrophils and eosinophils present in a blood sample aliquot, comprising the steps of:
   incubating the blood sample with a mixture of fluorochrome-conjugated monoclonal antibodies directed against the CD45, CD61, CD55 and CD59 cell surface proteins;
   measuring the intensity of the fluorescence emissions of the fluorochrome-conjugated monoclonal antibodies bound to the cells contained in said incubated blood sample;
   measuring the light scattering properties of the bound cells contained in said incubated blood sample;
   identifying the different subsets of red cells, platelets, lymphocytes, monocytes, neutrophils and eosinophils present in said blood sample based on their differential expression of CD45 and CD61 and different quantities of both forward (FSC) and sideward (SSC) light scattering properties, and;
   simultaneously quantifying the expression of CD55 and CD59 for each of said blood cell subsets,
   wherein the CD45 and CD61 monoclonal antibodies are conjugated to the same fluorochrome and the CD55 and CD59 monoclonal antibodies are conjugated to a second and a third different fluorochromes.

2. The method according to claim 1, wherein said fluorochromes or fluorochrome tandems are selected from the groups consisting of fluorescein isothiocyanate (FITC), phycoerythrin (PE), peridinin Chlorophyl protein (PerCP), PE-cyanin5 (PE Cy5), PE-Cyanin7 (PE Cy7), allophycocyanin (APC), PE-Texas red and APC-Cy7.

3. The method of claim 1, wherein the monoclonal antibodies used to identify and distinguish between red cells, platelets, lymphocytes, monocytes, neutrophils and eosinophils include a mixture of CD61, CD45 and CD64 monoclonal antibodies.

4. The method according to claim 1 wherein the monoclonal antibodies used to identify and distinguish between red cells, platelets, lymphocytes, monocytes, neutrophils and eosinophils include a mixture of CD41, CD45 and CD64 monoclonal antibodies.

5. The method according to claim 1 wherein the monoclonal antibodies used to identify and distinguish between red cells, platelets, lymphocytes, monocytes, neutrophils and eosinophils include a mixture of CD42, CD45 and CD64 monoclonal antibodies.

6. The method according to claim 1 wherein, in addition to the expression of CD55 and CD59 on said cell subsets, the expression of CD14 on monocytes is also analyzed.

7. The method according to claim 1 wherein, in addition to the expression of CD55 and CD59 on said cell subsets, the expression of CD24 on neutrophils and lymphocytes is also analyzed.

8. The method according to claim 1 wherein, in addition to the expression of CD55 and CD59 on said cell subsets, the expression of CD16 on neutrophils is also analyzed.

9. The method according to claim 1 wherein, in addition to the expression of CD55 and CD59 on said cell subsets, the expression of CD66bce on neutrophils is also analyzed.

10. The method according to claim 1 wherein, in addition to the expression of CD55 and CD59 on said cell subsets, the expression of CD48 on lymphocytes and monocytes is also analyzed.

11. The method according to claim 1 wherein, in addition to the expression of CD55 and CD59 on said cell subsets, the expression of CD52 on lymphocytes, monocytes, neutrophils and eosinophils is also analyzed.

12. The method according to claim 1 wherein, in addition to the expression of CD55 and CD59 on said cell subsets, the expression of CD58 on lymphocytes, monocytes, neutrophils and eosinophils is also analyzed.

13. The method according to claim 1 wherein, in addition to the expression of CD55 and CD59 on said cell subsets, the expression of CD73 on lymphocytes, is also analyzed.

14. The method according to claim 1 wherein, in addition to the expression of CD55 and CD59 on said cell subsets, the expression of CD87 on monocytes, and neutrophils is also analyzed.

15. The method according to claim 1 wherein, in addition to the expression of CD55 and CD59 on said cell subsets, the expression of CD90 on lymphocytes, is also analyzed.

16. The method according to claim 1 wherein, in addition to the expression of CD55 and CD59 on said cell subsets, the expression of CD 108 on lymphocytes, monocytes, neutrophils and eosinophils is also analyzed.

17. The method according to claim 1 wherein, in addition to the expression of CD55 and CD59 on said cell subsets, the expression of CD 109 on monocytes, neutrophils and eosinophils is also analyzed.

18. The method according to claim 1 wherein, in addition to the expression of CD55 and CD59 on said cell subsets, the expression of CD 157 on monocytes, and neutrophils is also analyzed.

* * * * *